(12) United States Patent
Thompson

(10) Patent No.: US 12,351,835 B1
(45) Date of Patent: Jul. 8, 2025

(54) COMPOSITION FOR REGULATING PRODUCTION OF PROTEINS

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

(21) Appl. No.: 18/889,088

(22) Filed: Sep. 18, 2024

(51) Int. Cl.
*C12N 9/12* (2006.01)
*C12N 15/86* (2006.01)

(52) U.S. Cl.
CPC ........... *C12N 9/1276* (2013.01); *C12N 15/86* (2013.01); *C12Y 207/07049* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 7,262,288 B1 * | 8/2007 | Cech | C12Y 207/07049 435/320.1 |
| 11,530,423 B1 * | 12/2022 | Thompson | C12N 15/86 |

* cited by examiner

*Primary Examiner* — Marsha Tsay
(74) *Attorney, Agent, or Firm* — Gowling WLG (Canada) LLP

(57) ABSTRACT

Some embodiments of the present disclosure relate to one or more compositions that upregulate the production of one or more sequences of mRNA. The sequences of mRNA may encode for translation of a target biomolecule, thereby causing an increase in bioavailability of the target biomolecule within a subject that is administered the one or more compositions. In some embodiments of the present disclosure, the target biomolecule is a protein such as TERT.

6 Claims, No Drawings

Specification includes a Sequence Listing.

COMPOSITION FOR REGULATING PRODUCTION OF PROTEINS

This application contains a Sequence Listing electronically submitted via Patent Center to the United States Patent and Trademark Office as an XML Document file entitled "A8149787US-SequenceListing.xml" created on 2024 Sep. 12 and having a size of 20,408 bytes. The information contained in the Sequence Listing is incorporated by reference herein.

TECHNICAL FIELD

The present disclosure generally relates to compositions for regulating the production of proteins. In particular, the present disclosure relates to compositions for regulating gene expression and, consequently, the production of proteins that act as transcriptional co-regulating factors.

BACKGROUND

Mutations and deletions can cause mis-expression of genes.

As such, it may be desirable to establish therapies, treatments and/or interventions that correct the misexpression of specific genes that have been subjected to mutations or deletions.

SUMMARY

Some embodiments of the present disclosure relate to one or more compositions that upregulate the production of one or more sequences of mRNA. The sequences of mRNA may encode for translation of a target biomolecule, thereby causing an increase in bioavailability of the target biomolecule within a subject that is administered the one or more compositions. In some embodiments of the present disclosure, the target biomolecule is a protein such as telomerase reverse transcriptase (TERT).

In some embodiments of the present disclosure the compositions comprise a plasmid of deoxyribonucleic acid (DNA) that includes one or more insert sequences of nucleotides that encode for the production of mRNA that encodes for the target biomolecule protein, which may also be referred to herein as target mRNA, and a backbone sequence of nucleotides that facilitates introduction of the one or more insert sequences into one or more of a subject's cells where it is expressed and/or replicated, resulting in an increase in target mRNA expression. Expression of the one or more insert sequences by one or more cells of the subject results in an increased production of the target mRNA and, consequently, increased translation of the target biomolecule by one or more of the subject's cells.

Some embodiments of the present disclosure relate to a recombinant plasmid (RP). In some embodiments of the present disclosure, the RP comprises a nucleotide sequence of SEQ ID NO. 1 and SEQ ID NO. 2. The RP comprises a nucleotide sequence encoding one or more nucleotide sequences encoding an mRNA sequence that encodes for the TERT protein.

Some embodiments of the present disclosure relate to a method of making a composition/target cell complex. The method comprising a step of administering a RP comprising SEQ ID NO. 1 and SEQ ID NO. 2 to a target cell for forming the composition/target cell complex, wherein the composition/target cell complex causes the target cell to increase production of one or more sequences of target mRNA that increases production of a target biomolecule.

Embodiments of the present disclosure relate to at least one approach for inducing endogenous production of one or more sequences of mRNA that encodes for a target biomolecule, for example TERT. A first approach utilizes gene vectors containing nucleotide sequences for increasing the endogenous production of one or more sequences of mRNA, which are complete or partial sequences and/or combinations thereof of TERT, which can be administered to a subject to increase the subject's production of one or more sequences of the mRNA.

DETAILED DESCRIPTION

Unless defined otherwise, all technical and scientific terms used therein have the meanings that would be commonly understood by one of skill in the art in the context of the present description. Although any methods and materials similar or equivalent to those described therein can also be used in the practice or testing of the present disclosure, the preferred compositions, methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "ameliorate" refers to improve and/or to make better and/or to make more satisfactory.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the one or more target cells' production of one or more proteins, and/or any post-translational modifications of one or more proteins.

As used therein, the term "composition" refers to a substance that, when administered to a subject, causes one or more chemical reactions and/or one or more physical reactions and/or one or more physiological reactions and/or one or more immunological reactions in the subject. In some embodiments of the present disclosure, the composition is a plasmid vector.

As used therein, the term "endogenous" refers to the production and/or modification of a molecule that originates within a subject.

As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target biomolecule" refers to a protein molecule that is found within a subject.

As used therein, the term "target cell" refers to one or more cells and/or cell types that are affected, either directly or indirectly, by a biomolecule.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, a composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus vector.

In some embodiments of the present disclosure, the insert comprises one or more nucleotide sequences that encode for production of at least one sequence of mRNA that increases the production of target biomolecules, such as a protein.

In some embodiments of the present disclosure, the target biomolecule is TERT.

Some embodiments of the present disclosure relate to a composition that can be administered to a subject with a condition that results, directly or indirectly, from the dysregulated production of a biomolecule. When a therapeutically effective amount of the composition is administered to the subject, the subject may change production and/or functionality of one or more biomolecules.

In some embodiments of the present disclosure, the subject may respond to receiving the therapeutic amount of the composition by changing production and/or functionality of one or more intermediary molecules by changing production of one or more DNA sequences, one or more RNA sequences, and/or one or more proteins that regulate the levels and/or functionality of the one or more intermediary molecules. The one or more intermediary molecules regulate the subject's levels and/or functionality of the one or more biomolecules.

In some embodiments of the present disclosure, administering a therapeutic amount of the composition to a subject upregulates the production, functionality or both one or more sequences of mRNA that each encode for one or more biomolecules.

In some embodiments of the present disclosure, the composition is an RP that may be used for gene therapy. The gene therapy is useful for increasing the subject's endogenous production of one or more sequences of mRNA that encode for a target biomolecule. For example, the RP can contain one or more nucleotide sequences that cause increased production of one or more nucleotide sequences that cause an increased production of one or more mRNA sequences that encode for one biomolecule, such as TERT.

In some embodiments of the present disclosure, the delivery vehicle of the RP used for gene therapy may be a vector that comprises a virus that can be enveloped, or not (unenveloped), replication effective or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus Dependoparvovirus. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle of the RP used for gene therapy may be a protein coat.

In some embodiments of the present disclosure, the delivery vehicle of the RP used for gene therapy may be a lipid vesicle.

The embodiments of the present disclosure also relate to administering a therapeutically effective amount of the composition. In some embodiments of the present disclosure, the therapeutically effective amount of the composition that is administered to a patient is between about 10 and about $1\times10^{16}$ TCID$_{50}$/kg (50% tissue culture infective dose per kilogram of the patient's body mass). In some embodiments of the present disclosure, the therapeutically effective amount of the composition that is administered to the patient is about $1\times10^{13}$ TCID$_{50}$/kg. In some embodiments of the present disclosure, the therapeutically effective amount of the composition that is administered to a patient is measured in TPC/kg (total particle count of the composition per kilogram of the patient's body mass). In some embodiments of the present disclosure, the therapeutically effective amount of the composition is between about 10 and about $1\times10^{16}$ TCP/kg.

Some embodiments of the present disclosure relate to an adeno-associated virus (AAV) genome consisting of a RP that when operable inside a target cell will cause the target cell to produce a mRNA sequence that upregulates production of a biomolecule, with an example being TERT. The RP is comprised of AAV2 inverted terminal repeats (ITRs), a composite CASI promoter, and a human growth hormone (HGH) signal peptide followed by a mRNA expression cassette encoding for TERT, followed by a Woodchuck Hepatitis Virus post-transcriptional regulatory element (WPRE) and a Simian virus 40 (SV40) polyadenylation (polyA) signal.

SEQ ID NO. 1 (backbone sequence No. 1):
5'

TTCTAGAAAGATCTAACTTGTTTATTGCAGCTTATAATGGTTACAAATAAAGCAATA

GCATCACAAATTTCACAAATAAAGCATTTTTTTCACTGCATTCTAGTTGTGGTTTGTC

CAAACTCATCAATGTATCTTATCATGTCTGGATCTCGACCTCGACTAGAGCATGGCT

ACGTAGATAAGTAGCATGGCGGGTTAATCATTAACTACAAGGAACCCCTAGTGATG

GAGTTGGCCACTCCCTCTCTGCGCGCTCGCTCGCTCACTGAGGCCGGGCGACCAAAG

GTCGCCCGACGCCCGGGCTTTGCCCGGGCGGCCTCAGTGAGCGAGCGAGCGCGCAG

CTGGCGTAATAGCGAAGAGGCCCGCACCGATCGCCCTTCCCAACAGTTGCGCAGCC

TGAATGGCGAATGGCGATTCCGTTGCAATGGCTGGCGGTAATATTGTTCTGGATATT

ACCAGCAAGGCCGATAGTTTGAGTTCTTCTACTCAGGCAAGTGATGTTATTACTAAT

CAAAGAAGTATTGCGACAACGGTTAATTTGCGTGATGGACAGACTCTTTTACTCGGT

GGCCTCACTGATTATAAAAACACTTCTCAGGATTCTGGCGTACCGTTCCTGTCTAAA

ATCCCTTTAATCGGCCTCCTGTTTAGCTCCCGCTCTGATTCTAACGAGGAAAGCACGT

TATACGTGCTCGTCAAAGCAACCATAGTACGCGCCCTGTAGCGGCGCATTAAGCGC

GGCGGGTGTGGTGGTTACGCGCAGCGTGACCGCTACACTTGCCAGCGCCCTAGCGC

CCGCTCCTTTCGCTTTCTTCCCTTCCTTTCTCGCCACGTTCGCCGGCTTTCCCCGTCAA

GCTCTAAATCGGGGGCTCCCTTTAGGGTTCCGATTTAGTGCTTTACGGCACCTCGAC

CCCAAAAAACTTGATTAGGGTGATGGTTCACGTAGTGGGCCATCGCCCTGATAGACG

GTTTTTCGCCCTTTGACGTTGGAGTCCACGTTCTTTAATAGTGGACTCTTGTTCCAAA

CTGGAACAACACTCAACCCTATCTCGGTCTATTCTTTTGATTTATAAGGGATTTTGCC

GATTTCGGCCTATTGGTTAAAAAATGAGCTGATTTAACAAAAATTTAACGCGAATTT

TAACAAAATATTAACGTTTACAATTTAAATATTTGCTTATACAATCTTCCTGTTTTTG

GGGCTTTTCTGATTATCAACCGGGGTACATATGATTGACATGCTAGTTTTACGATTAC

CGTTCATCGATTCTCTTGTTTGCTCCAGACTCTCAGGCAATGACCTGATAGCCTTTGT

AGAGACCTCTCAAAAATAGCTACCCTCTCCGGCATGAATTTATCAGCTAGAACGGTT

GAATATCATATTGATGGTGATTTGACTGTCTCCGGCCTTTCTCACCCGTTTGAATCTT

TACCTACACATTACTCAGGCATTGCATTTAAAATATATGAGGGTTCTAAAAATTTTT

ATCCTTGCGTTGAAATAAAGGCTTCTCCCGCAAAAGTATTACAGGGTCATAATGTTT

TTGGTACAACCGATTTAGCTTTATGCTCTGAGGCTTTATTGCTTAATTTTGCTAATTC

-continued

```
TTTGCCTTGCCTGTATGATTTATTGGATGTTGGAATTCCTGATGCGGTATTTTCTCCTT

ACGCATCTGTGCGGTATTTCACACCGCATATGGTGCACTCTCAGTACAATCTGCTCT

GATGCCGCATAGTTAAGCCAGCCCCGACACCCGCCAACACCCGCTGACGCGCCCTG

ACGGGCTTGTCTGCTCCCGGCATCCGCTTACAGACAAGCTGTGACCGTCTCCGGAG

CTGCATGTGTCAGAGGTTTTCACCGTCATCACCGAAACGCGCGAGACGAAAGGGCC

TCGTGATACGCCTATTTTTATAGGTTAATGTCATGATAATAATGGTTTCTTAGACGTC

AGGTGGCACTTTTCGGGGAAATGTGCGCGGAACCCCTATTTGTTTATTTTTCTAAATA

CATTCAAATATGTATCCGCTCATGAGACAATAACCCTGATAAATGCTTCAATAATAT

TGAAAAAGGAAGAGTATGAGTATTCAACATTTCCGTGTCGCCCTTATTCCCTTTTTTG

CGGCATTTTGCCTTCCTGTTTTTGCTCACCCAGAAACGCTGGTGAAAGTAAAAGATG

CTGAAGATCAGTTGGGTGCACGAGTGGGTTACATCGAACTGGATCTCAACAGCGGT

AAGATCCTTGAGAGTTTTCGCCCCGAAGAACGTTTTCCAATGATGAGCACTTTTAAA

GTTCTGCTATGTGGCGCGGTATTATCCCGTATTGACGCCGGGCAAGAGCAACTCGGT

CGCCGCATACACTATTCTCAGAATGACTTGGTTGAGTACTCACCAGTCACAGAAAAG

CATCTTACGGATGGCATGACAGTAAGAGAATTATGCAGTGCTGCCATAACCATGAGT

GATAACACTGCGGCCAACTTACTTCTGACAACGATCGGAGGACCGAAGGAGCTAAC

CGCTTTTTTGCACAACATGGGGGATCATGTAACTCGCCTTGATCGTTGGGAACCGGA

GCTGAATGAAGCCATACCAAACGACGAGCGTGACACCACGATGCCTGTAGCAATGG

CAACAACGTTGCGCAAACTATTAACTGGCGAACTACTTACTCTAGCTTCCCGGCAAC

AATTAATAGACTGGATGGAGGCGGATAAAGTTGCAGGACCACTTCTGCGCTCGGCC

CTTCCGGCTGGCTGGTTTATTGCTGATAAATCTGGAGCCGGTGAGCGTGGGTCTCGC

GGTATCATTGCAGCACTGGGGCCAGATGGTAAGCCCTCCCGTATCGTAGTTATCTAC

ACGACGGGGAGTCAGGCAACTATGGATGAACGAAATAGACAGATCGCTGAGATAG

GTGCCTCACTGATTAAGCATTGGTAACTGTCAGACCAAGTTTACTCATATATACTTTA

GATTGATTTAAAACTTCATTTTTAATTTAAAAGGATCTAGGTGAAGATCCTTTTTGAT

AATCTCATGACCAAAATCCCTTAACGTGAGTTTTCGTTCCACTGAGCGTCAGACCCC

GTAGAAAAGATCAAAGGATCTTCTTGAGATCCTTTTTTTCTGCGCGTAATCTGCTGCT

TGCAAACAAAAAAACCACCGCTACCAGCGGTGGTTTGTTTGCCGGATCAAGAGCTA

CCAACTCTTTTTCCGAAGGTAACTGGCTTCAGCAGAGCGCAGATACCAAATACTGTC

CTTCTAGTGTAGCCGTAGTTAGGCCACCACTTCAAGAACTCTGTAGCACCGCCTACA

TACCTCGCTCTGCTAATCCTGTTACCAGTGGCTGCTGCCAGTGGCGATAAGTCGTGT

CTTACCGGGTTGGACTCAAGACGATAGTTACCGGATAAGGCGCAGCGGTCGGGCTG

AACGGGGGGTTCGTGCACACAGCCCAGCTTGGAGCGAACGACCTACACCGAACTGA

GATACCTACAGCGTGAGCTATGAGAAAGCGCCACGCTTCCCGAAGGGAGAAAGGCG

GACAGGTATCCGGTAAGCGGCAGGGTCGGAACAGGAGAGCGCACGAGGGAGCTTC

CAGGGGGAAACGCCTGGTATCTTTATAGTCCTGTCGGGTTTCGCCACCTCTGACTTG

AGCGTCGATTTTTGTGATGCTCGTCAGGGGGCGGAGCCTATGGAAAAACGCCAGC

AACGCGGCCTTTTTACGGTTCCTGGCCTTTTGCTGGCCTTTTGCTCACATGTTCTTTCC

TGCGTTATCCCCTGATTCTGTGGATAACCGTATTACCGCCTTTGAGTGAGCTGATACC

GCTCGCCGCAGCCGAACGACCGAGCGCAGCGAGTCAGTGAGCGAGGAAGCGGAAG
```

-continued

```
AGCGCCCAATACGCAAACCGCCTCTCCCCGCGCGTTGGCCGATTCATTAATGCAGCT
GCGCGCTCGCTCGCTCACTGAGGCCGCCCGGGCAAAGCCCGGGCGTCGGGCGACCT
TTGGTCGCCCGGCCTCAGTGAGCGAGCGAGCGCGCAGAGAGGGAGTGGCCAACTCC
ATCACTAGGGGTTCCTTGTAGTTAATGATTAACCCGCCATGCTACTTATCTACGTAGC
CATGCTCTAGGACATTGATTATTGACTAGTGGAGTTCCGCGTTACATAACTTACGGT
AAATGGCCCGCCTGGCTGACCGCCCAACGACCCCCGCCCATTGACGTCAATAATGA
CGTATGTTCCCATAGTAACGCCAATAGGGACTTTCCATTGACGTCAATGGGTGGAGT
ATTTACGGTAAACTGCCCACTTGGCAGTACATCAAGTGTATCATATGCCAAGTACGC
CCCCTATTGACGTCAATGACGGTAAATGGCCCGCCTGGCATTATGCCCAGTACATGA
CCTTATGGGACTTTCCTACTTGGCAGTACATCTACGTATTAGTCATCGCTATTACCAT
GGTCGAGGTGAGCCCCACGTTCTGCTTCACTCTCCCCATCTCCCCCCCCTCCCCACCC
CCAATTTTGTATTTATTTATTTTTTAATTATTTTGTGCAGCGATGGGGGCGGGGGGGG
GGGGGGCGCGCCAGGCGGGGCGGGCGGGGCGAGGGGCGGGGCGGGGCGAG
GCGGAGAGGTGCGGCGGCAGCCAATCAGAGCGGCGCGCTCCGAAAGTTTCCTTTTA
TGGCGAGGCGGCGGCGGCGGCGGCCCTATAAAAAGCGAAGCGCGCGGCGGGCGGG
AGTCGCTGCGCGCTGCCTTCGCCCCGTGCCCCGCTCCGCCGCCGCCTCGCGCCGCCC
GCCCCGGCTCTGACTGACCGCGTTACTAAAACAGGTAAGTCCGGCCTCCGCGCCGG
GTTTTGGCGCCTCCCGCGGGCGCCCCCCTCCTCACGGCGAGCGCTGCCACGTCAGAC
GAAGGGCGCAGCGAGCGTCCTGATCCTTCCGCCCGGACGCTCAGGACAGCGGCCCG
CTGCTCATAAGACTCGGCCTTAGAACCCCAGTATCAGCAGAAGGACATTTTAGGACG
GGACTTGGGTGACTCTAGGGCACTGGTTTTCTTTCCAGAGAGCGGAACAGGCGAGG
AAAAGTAGTCCCTTCTCGGCGATTCTGCGGAGGGATCTCCGTGGGGCGGTGAACGCC
GATGATGCCTCTACTAACCATGTTCATGTTTTCTTTTTTTTTCTACAGGTCCTGGGTG
ACGAACAGGGTACCGCCACC
```
3'

SEQ ID NO. 2 (mRNA expression cassette No. 2 - TERT):
5'

```
ATGCCGCGCGCGCCGCGCTGCCGCGCGGTGCGCAGCCTGCTGCGCAGCCATTATCGC
GAAGTGCTGCCGCTGGCGACCTTTGTGCGCCGCCTGGGCCCGCAGGGCTGGCGCCTG
GTGCAGCGCGGCGATCCGGCGGCGTTTCGCGCGCTGGTGGCGCAGTGCCTGGTGTG
CGTGCCGTGGGATGCGCGCCCGCCGCCGGCGGCGCCGAGCTTTCGCCAGGTGAGCT
GCCTGAAAGAACTGGTGGCGCGCGTGCTGCAGCGCCTGTGCGAACGCGGCGCGAAA
AACGTGCTGGCGTTTGGCTTTGCGCTGCTGGATGGCGCGCGCGGCGGCCCGCCGGA
AGCGTTTACCACCAGCGTGCGCAGCTATCTGCCGAACACCGTGACCGATGCGTGCGC
GGCAGCGGCGCGTGGGGCCTGCTGCTGCGCCGCGTGGGCGATGATGTGCTGGTGCA
TCTGCTGGCGCGCTGCGCGCTGTTTGTGCTGGTGGCGCCGAGCTGCGCGTATCAGGT
GTGCGGCCCGCCGCTGTATCAGCTGGGCGCGGCGACCCAGGCGCGCCCGCCGCCGC
ATGCGAGCGGCCCGCGCCGCCGCCTGGGCTGCGAACGCGCGTGGAACCATAGCGTG
CGCGAAGCGGGCGTGCCGCTGGGCCTGCCGGCGCCGGGCGCGCGCCGCCGCGGCGG
CAGCGCGAGCCGCAGCCTGCCGCTGCCGAAACGCCCGCGCCGCGGCGCGGCGCCGG
```

-continued

```
AACCGGAACGCACCCCGGTGGGCCAGGGCAGCTGGGCGCATCCGGGCCGCACCCGC

GGCCCGAGCGATCGCGGCTTTTGCGTGGTGAGCCCGGCGCGCCCGGCGGAAGAAGC

GACCAGCCTGGAAGGCGCGCTGAGCGGCACCCGCCATAGCCATCCGAGCGTGGGCC

GCCAGCATCATGCGGGCCCGCCGAGCACCAGCCGCCCGCCGCGCCCGTGGGATACC

CCGTGCCCGCCGGTGTATGCGGAAACCAAACATTTTCTGTATAGCAGCGGCGATAAA

GAACAGCTGCGCCCGAGCTTTCTGCTGAGCAGCCTGCGCCCGAGCCTGACCGGCGC

GCGCCGCCTGGTGGAAACCATTTTTCTGGGCAGCCGCCCGTGGATGCCGGGCACCCC

GCGCCGCCTGCCGCGCCTGCCGCAGCGCTATTGGCAGATGCGCCCGCTGTTTCTGGA

ACTGCTGGGCAACCATGCGCAGTGCCCGTATGGCGTGCTGCTGAAAACCCATTGCCC

GCTGCGCGCGGCGGTGACCCCGGCGGCGGGCGTGTGCGCGCGCGAAAAACCGCAGG

GCAGCGTGGCGGCGCCGGAAGAAGAAGATACCGATCCGCGCCGCCTGGTGCAGCTG

CTGCGCCAGCATAGCAGCCCGTGGCAGGTGTATGGCTTTGTGCGCGCGTGCCTGCGC

CGCCTGGTGCCGCCGGGCCTGTGGGGCAGCCGCCATAACGAACGCCGCTTTCTGCGC

AACACCAAAAAATTTATTAGCCTGGGCAAACATGCGAAACTGAGCCTGCAGGAACT

GACCTGGAAAATGAGCGTGCGCGATTGCGCGTGGCTGCGCCGCAGCCCGGGCGTGG

GCTGCGTGCCGGCGGCGGAACATCGCCTGCGCGAAGAAATTCTGGCGAAATTTCTG

CATTGGCTGATGAGCGTGTATGTGGTGGAACTGCTGCGCAGCTTTTTTTATGTGACC

GAAACCACCTTTCAGAAAAACCGCCTGTTTTTTTATCGCAAAAGCGTGTGGAGCAAA

CTGCAGAGCATTGGCATTCGCCAGCATCTGAAACGCGTGCAGCTGCGCGAACTGAG

CGAAGCGGAAGTGCGCCAGCATCGCGAAGCGCGCCCGGCGCTGCTGACCAGCCGCC

TGCGCTTTATTCCGAAACCGGATGGCCTGCGCCCGATTGTGAACATGGATTATGTGG

TGGGCGCGCGCACCTTTCGCCGCGAAAAACGCGCGGAACGCCTGACCAGCCGCGTG

AAAGCGCTGTTTAGCGTGCTGAACTATGAACGCGCGCGCCGCCCGGGCCTGCTGGG

CGCGAGCGTGCTGGGCCTGGATGATATTCATCGCGCGTGGCGCACCTTTGTGCTGCG

CGTGCGCGCGCAGGATCCGCCGCCGGAACTGTATTTTGTGAAAGTGGATGTGACCG

GCGCGTATGATACCATTCCGCAGGATCGCCTGACCGAAGTGATTGCGAGCATTATTA

AACCGCAGAACACCTATTGCGTGCGCCGCTATGCGGTGGTGCAGAAAGCGGCGCAT

GGCCATGTGCGCAAAGCGTTTAAAAGCCATGTGAGCACCCTGACCGATCTGCAGCC

GTATATGCGCCAGTTTGTGGCGCATCTGCAGGAAACCAGCCCGCTGCGCGATGCGGT

GGTGATTGAACAGAGCAGCAGCCTGAACGAAGCGAGCAGCGGCCTGTTTGATGTGT

TTCTGCGCTTTATGTGCCATCATGCGGTGCGCATTCGCGGCAAAAGCTATGTGCAGT

GCCAGGGCATTCCGCAGGGCAGCATTCTGAGCACCCTGCTGTGCAGCCTGTGCTATG

GCGATATGGAAAACAAACTGTTTGCGGGCATTCGCCGCGATGGCCTGCTGCTGCGCC

TGGTGGATGATTTTCTGCTGGTGACCCCGCATCTGACCCATGCGAAAACCTTTCTGC

GCACCCTGGTGCGCGGCGTGCCGGAATATGGCTGCGTGGTGAACCTGCGCAAAACC

GTGGTGAACTTTCCGGTGGAAGATGAAGCGCTGGGCGGCACCGCGTTTGTGCAGAT

GCCGGCGCATGGCCTGTTTCCGTGGTGCGGCCTGCTGCTGGATACCCGCACCCTGGA

AGTGCAGAGCGATTATAGCAGCTATGCGCGCACCAGCATTCGCGCGAGCCTGACCT

TTAACCGCGGCTTTAAAGCGGGCCGCAACATGCGCCGCAAACTGTTTGGCGTGCTGC

GCCTGAAATGCCATAGCCTGTTTCTGGATCTGCAGGTGAACAGCCTGCAGACCGTGT
```

-continued
```
GCACCAACATTTATAAAATTCTGCTGCTGCAGGCGTATCGCTTTCATGCGTGCGTGC

TGCAGCTGCCGTTTCATCAGCAGGTGTGGAAAAACCCGACCTTTTTTCTGCGCGTGA

TTAGCGATACCGCGAGCCTGTGCTATAGCATTCTGAAAGCGAAAAACGCGGGCATG

AGCCTGGGCGCGAAAGGCGCGGCGGGCCCGCTGCCGAGCGAAGCGGTGCAGTGGCT

GTGCCATCAGGCGTTTCTGCTGAAACTGACCCGCCATCGCGTGACCTATGTGCCGCT

GCTGGGCAGCCTGCGCACCGCGCAGACCCAGCTGAGCCGCAAACTGCCGGGCACCA

CCCTGACCGCGCTGGAAGCGGCGGCGAACCCGGCGCTGCCGAGCGATTTTAAAACC

ATTCTGGAT

3'

SEQ ID NO: 3 = SEQ ID NO: 1 + SEQ ID NO: 2
5'

TTCTAGAAAGATCTAACTTGTTTATTGCAGCTTATAATGGTTACAAATAAAGCAATA

GCATCACAAATTTCACAAATAAAGCATTTTTTTCACTGCATTCTAGTTGTGGTTTGTC

CAAACTCATCAATGTATCTTATCATGTCTGGATCTCGACCTCGACTAGAGCATGGCT

ACGTAGATAAGTAGCATGGCGGGTTAATCATTAACTACAAGGAACCCCTAGTGATG

GAGTTGGCCACTCCCTCTCTGCGCGCTCGCTCGCTCACTGAGGCCGGGCGACCAAAG

GTCGCCCGACGCCCGGGCTTTGCCCGGGCGGCCTCAGTGAGCGAGCGAGCGCGCAG

CTGGCGTAATAGCGAAGAGGCCCGCACCGATCGCCCTTCCCAACAGTTGCGCAGCC

TGAATGGCGAATGGCGATTCCGTTGCAATGGCTGGCGGTAATATTGTTCTGGATATT

ACCAGCAAGGCCGATAGTTTGAGTTCTTCTACTCAGGCAAGTGATGTTATTACTAAT

CAAAGAAGTATTGCGACAACGGTTAATTTGCGTGATGGACAGACTCTTTTACTCGGT

GGCCTCACTGATTATAAAAACACTTCTCAGGATTCTGGCGTACCGTTCCTGTCTAAA

ATCCCTTTAATCGGCCTCCTGTTTAGCTCCCGCTCTGATTCTAACGAGGAAAGCACGT

TATACGTGCTCGTCAAAGCAACCATAGTACGCGCCCTGTAGCGGCGCATTAAGCGC

GGCGGGTGTGGTGGTTACGCGCAGCGTGACCGCTACACTTGCCAGCGCCCTAGCGC

CCGCTCCTTTCGCTTTCTTCCCTTCCTTTCTCGCCACGTTCGCCGGCTTTCCCCGTCAA

GCTCTAAATCGGGGGCTCCCTTTAGGGTTCCGATTTAGTGCTTTACGGCACCTCGAC

CCCAAAAAACTTGATTAGGGTGATGGTTCACGTAGTGGGCCATCGCCCTGATAGACG

GTTTTTCGCCCTTTGACGTTGGAGTCCACGTTCTTTAATAGTGGACTCTTGTTCCAAA

CTGGAACAACACTCAACCCTATCTCGGTCTATTCTTTTGATTTATAAGGGATTTTGCC

GATTTCGGCCTATTGGTTAAAAAATGAGCTGATTTAACAAAAATTTAACGCGAATTT

TAACAAAATATTAACGTTTACAATTTAAATATTTGCTTATACAATCTTCCTGTTTTTG

GGGCTTTTCTGATTATCAACCGGGGTACATATGATTGACATGCTAGTTTTACGATTAC

CGTTCATCGATTCTCTTGTTTGCTCCAGACTCTCAGGCAATGACCTGATAGCCTTTGT

AGAGACCTCTCAAAAATAGCTACCCTCTCCGGCATGAATTTATCAGCTAGAACGGTT

GAATATCATATTGATGGTGATTTGACTGTCTCCGGCCTTTCTCACCCGTTTGAATCTT

TACCTACACATTACTCAGGCATTGCATTTAAAATATATGAGGGTTCTAAAAATTTTT

ATCCTTGCGTTGAAATAAAGGCTTCTCCCGCAAAAGTATTACAGGGTCATAATGTTT

TTGGTACAACCGATTTAGCTTTATGCTCTGAGGCTTTATTGCTTAATTTTGCTAATTC

TTTGCCTTGCCTGTATGATTTATTGGATGTTGGAATTCCTGATGCGGTATTTTCTCCTT
```

-continued

```
ACGCATCTGTGCGGTATTTCACACCGCATATGGTGCACTCTCAGTACAATCTGCTCT
GATGCCGCATAGTTAAGCCAGCCCCGACACCCGCCAACACCCGCTGACGCGCCCTG
ACGGGCTTGTCTGCTCCCGGCATCCGCTTACAGACAAGCTGTGACCGTCTCCGGGAG
CTGCATGTGTCAGAGGTTTTCACCGTCATCACCGAAACGCGCGAGACGAAAGGGCC
TCGTGATACGCCTATTTTTATAGGTTAATGTCATGATAATAATGGTTTCTTAGACGTC
AGGTGGCACTTTTCGGGGAAATGTGCGCGGAACCCCTATTTGTTTATTTTTCTAAATA
CATTCAAATATGTATCCGCTCATGAGACAATAACCCTGATAAATGCTTCAATAATAT
TGAAAAAGGAAGAGTATGAGTATTCAACATTTCCGTGTCGCCCTTATTCCCTTTTTG
CGGCATTTTGCCTTCCTGTTTTTGCTCACCCAGAAACGCTGGTGAAAGTAAAAGATG
CTGAAGATCAGTTGGGTGCACGAGTGGGTTACATCGAACTGGATCTCAACAGCGGT
AAGATCCTTGAGAGTTTTCGCCCCGAAGAACGTTTTCCAATGATGAGCACTTTTAAA
GTTCTGCTATGTGGCGCGGTATTATCCCGTATTGACGCCGGGCAAGAGCAACTCGGT
CGCCGCATACACTATTCTCAGAATGACTTGGTTGAGTACTCACCAGTCACAGAAAAG
CATCTTACGGATGGCATGACAGTAAGAGAATTATGCAGTGCTGCCATAACCATGAGT
GATAACACTGCGGCCAACTTACTTCTGACAACGATCGGAGGACCGAAGGAGCTAAC
CGCTTTTTTGCACAACATGGGGGATCATGTAACTCGCCTTGATCGTTGGGAACCGGA
GCTGAATGAAGCCATACCAAACGACGAGCGTGACACCACGATGCCTGTAGCAATGG
CAACAACGTTGCGCAAACTATTAACTGGCGAACTACTTACTCTAGCTTCCCGGCAAC
AATTAATAGACTGGATGGAGGCGGATAAAGTTGCAGGACCACTTCTGCGCTCGGCC
CTTCCGGCTGGCTGGTTTATTGCTGATAAATCTGGAGCCGGTGAGCGTGGGTCTCGC
GGTATCATTGCAGCACTGGGGCCAGATGGTAAGCCCTCCCGTATCGTAGTTATCTAC
ACGACGGGGAGTCAGGCAACTATGGATGAACGAAATAGACAGATCGCTGAGATAG
GTGCCTCACTGATTAAGCATTGGTAACTGTCAGACCAAGTTTACTCATATATACTTTA
GATTGATTTAAAACTTCATTTTTAATTTAAAAGGATCTAGGTGAAGATCCTTTTTGAT
AATCTCATGACCAAAATCCCTTAACGTGAGTTTTCGTTCCACTGAGCGTCAGACCCC
GTAGAAAAGATCAAAGGATCTTCTTGAGATCCTTTTTTTCTGCGCGTAATCTGCTGCT
TGCAAACAAAAAAACCACCGCTACCAGCGGTGGTTTGTTTGCCGGATCAAGAGCTA
CCAACTCTTTTTCCGAAGGTAACTGGCTTCAGCAGAGCGCAGATACCAAATACTGTC
CTTCTAGTGTAGCCGTAGTTAGGCCACCACTTCAAGAACTCTGTAGCACCGCCTACA
TACCTCGCTCTGCTAATCCTGTTACCAGTGGCTGCTGCCAGTGGCGATAAGTCGTGT
CTTACCGGGTTGGACTCAAGACGATAGTTACCGGATAAGGCGCAGCGGTCGGGCTG
AACGGGGGGTTCGTGCACACAGCCCAGCTTGGAGCGAACGACCTACACCGAACTGA
GATACCTACAGCGTGAGCTATGAGAAAGCGCCACGCTTCCCGAAGGGAGAAAGGCG
GACAGGTATCCGGTAAGCGGCAGGGTCGGAACAGGAGAGCGCACGAGGGAGCTTC
CAGGGGGAAACGCCTGGTATCTTTATAGTCCTGTCGGGTTTCGCCACCTCTGACTTG
AGCGTCGATTTTTGTGATGCTCGTCAGGGGGCGGAGCCTATGGAAAAACGCCAGC
AACGCGGCCTTTTTACGGTTCCTGGCCTTTTGCTGGCCTTTTGCTCACATGTTCTTTCC
TGCGTTATCCCCTGATTCTGTGGATAACCGTATTACCGCCTTTGAGTGAGCTGATACC
GCTCGCCGCAGCCGAACGACCGAGCGCAGCGAGTCAGTGAGCGAGGAAGCGGAAG
AGCGCCCAATACGCAAACCGCCTCTCCCCGCGCGTTGGCCGATTCATTAATGCAGCT
```

-continued

```
GCGCGCTCGCTCGCTCACTGAGGCCGCCCGGGCAAAGCCCGGGCGTCGGGCGACCT

TTGGTCGCCCGGCCTCAGTGAGCGAGCGAGCGCGCAGAGAGGGAGTGGCCAACTCC

ATCACTAGGGGTTCCTTGTAGTTAATGATTAACCCGCCATGCTACTTATCTACGTAGC

CATGCTCTAGGACATTGATTATTGACTAGTGGAGTTCCGCGTTACATAACTTACGGT

AAATGGCCCGCCTGGCTGACCGCCCAACGACCCCCGCCCATTGACGTCAATAATGA

CGTATGTTCCCATAGTAACGCCAATAGGGACTTTCCATTGACGTCAATGGGTGGAGT

ATTTACGGTAAACTGCCCACTTGGCAGTACATCAAGTGTATCATATGCCAAGTACGC

CCCCTATTGACGTCAATGACGGTAAATGGCCCGCCTGGCATTATGCCCAGTACATGA

CCTTATGGGACTTTCCTACTTGGCAGTACATCTACGTATTAGTCATCGCTATTACCAT

GGTCGAGGTGAGCCCCACGTTCTGCTTCACTCTCCCCATCTCCCCCCCCTCCCCACCC

CCAATTTTGTATTTATTTATTTTTTAATTATTTTGTGCAGCGATGGGGGCGGGGGGGG

GGGGGGGCGCGCGCCAGGCGGGGCGGGGCGGGGCGAGGGGCGGGGCGGGGCGAG

GCGGAGAGGTGCGGCGGCAGCCAATCAGAGCGGCGCGCTCCGAAAGTTTCCTTTTA

TGGCGAGGCGGCGGCGGCGGCGGCCCTATAAAAAGCGAAGCGCGCGGCGGGCGGG

AGTCGCTGCGCGCTGCCTTCGCCCCGTGCCCCGCTCCGCCGCCGCCTCGCGCCGCCC

GCCCCGGCTCTGACTGACCGCGTTACTAAAACAGGTAAGTCCGGCCTCCGCGCCGG

GTTTTGGCGCCTCCCGCGGGCGCCCCCCTCCTCACGGCGAGCGCTGCCACGTCAGAC

GAAGGGCGCAGCGAGCGTCCTGATCCTTCCGCCCGGACGCTCAGGACAGCGGCCCG

CTGCTCATAAGACTCGGCCTTAGAACCCCAGTATCAGCAGAAGGACATTTTAGGACG

GGACTTGGGTGACTCTAGGGCACTGGTTTTCTTTCCAGAGAGCGGAACAGGCGAGG

AAAAGTAGTCCCTTCTCGGCGATTCTGCGGAGGGATCTCCGTGGGGCGGTGAACGCC

GATGATGCCTCTACTAACCATGTTCATGTTTTCTTTTTTTTTCTACAGGTCCTGGGTG

ACGAACAGGGTACCGCCACCATGCCGCGCGCCGCGCTGCCGCGCGGTGCGCAGC

CTGCTGCGCAGCCATTATCGCGAAGTGCTGCCGCTGGCGACCTTTGTGCGCCGCCTG

GGCCCGCAGGGCTGGCGCCTGGTGCAGCGCGGCGATCCGGCGGCGTTTCGCGCGCT

GGTGGCGCAGTGCCTGGTGTGCGTGCCGTGGGATGCGCGCCCGCCGCCGGCGGCGC

CGAGCTTTCGCCAGGTGAGCTGCCTGAAAGAACTGGTGGCGCGCGTGCTGCAGCGC

CTGTGCGAACGCGGCGCGAAAAACGTGCTGGCGTTTGGCTTTGCGCTGCTGGATGGC

GCGCGCGGCGGCCCGCCGGAAGCGTTTACCACCAGCGTGCGCAGCTATCTGCCGAA

CACCGTGACCGATGCGTGCGCGGCAGCGGCGCGTGGGCCTGCTGCTGCGCCGCGT

GGGCGATGATGTGCTGGTGCATCTGCTGGCGCGCTGCGCGCTGTTTGTGCTGGTGGC

GCCGAGCTGCGCGTATCAGGTGTGCGGCCCGCCGCTGTATCAGCTGGGCGCGGCGA

CCCAGGCGCGCCCGCCGCCGCATGCGAGCGGCCCGCGCCGCCGCCTGGGCTGCGAA

CGCGCGTGGAACCATAGCGTGCGCGAAGCGGGCGTGCCGCTGGGCCTGCCGGCGCC

GGGCGCGCGCCGCCGCGGCGGCAGCGCGAGCCGCAGCCTGCCGCTGCCGAAACGCC

CGCGCCGCGGCGCGGCGCCGGAACCGGAACGCACCCCGGTGGGCCAGGGCAGCTG

GGCGCATCCGGGCCGCACCCGCGGCCCGAGCGATCGCGGCTTTTGCGTGGTGAGCC

CGGCGCGCCCGGCGGAAGAAGCGACCAGCCTGGAAGGCGCGCTGAGCGGCACCCG

CCATAGCCATCCGAGCGTGGGCCGCCAGCATCATGCGGGCCCGCCGAGCACCAGCC

GCCCGCCGCGCCCGTGGGATACCCCGTGCCCGCCGGTGTATGCGGAAACCAAACAT

TTTCTGTATAGCAGCGGCGATAAAGAACAGCTGCGCCCGAGCTTTCTGCTGAGCAGC
```

-continued

```
CTGCGCCCGAGCCTGACCGGCGCGCGCCGCCTGGTGGAAACCATTTTTCTGGGCAGC
CGCCCGTGGATGCCGGGCACCCCGCGCCGCCTGCCGCGCCTGCCGCAGCGCTATTGG
CAGATGCGCCCGCTGTTTCTGGAACTGCTGGGCAACCATGCGCAGTGCCCGTATGGC
GTGCTGCTGAAAACCCATTGCCCGCTGCGCGCGGCGGTGACCCCGGCGGCGGGCGT
GTGCGCGCGCGAAAAACCGCAGGGCAGCGTGGCGGCGCCGGAAGAAGAAGATACC
GATCCGCGCCGCCTGGTGCAGCTGCTGCGCCAGCATAGCAGCCCGTGGCAGGTGTA
TGGCTTTGTGCGCGCGTGCCTGCGCCGCCTGGTGCCGCCGGGCCTGTGGGGCAGCCG
CCATAACGAACGCCGCTTTCTGCGCAACACCAAAAAATTTATTAGCCTGGGCAAAC
ATGCGAAACTGAGCCTGCAGGAACTGACCTGGAAAATGAGCGTGCGCGATTGCGCG
TGGCTGCGCCGCAGCCCGGGCGTGGGCTGCGTGCCGGCGGCGGAACATCGCCTGCG
CGAAGAAATTCTGGCGAAATTTCTGCATTGGCTGATGAGCGTGTATGTGGTGGAACT
GCTGCGCAGCTTTTTTTATGTGACCGAAACCACCTTTCAGAAAAACCGCCTGTTTTTT
TATCGCAAAAGCGTGTGGAGCAAACTGCAGAGCATTGGCATTCGCCAGCATCTGAA
ACGCGTGCAGCTGCGCGAACTGAGCGAAGCGGAAGTGCGCCAGCATCGCGAAGCGC
GCCCGGCGCTGCTGACCAGCCGCCTGCGCTTTATTCCGAAACCGGATGGCCTGCGCC
CGATTGTGAACATGGATTATGTGGTGGGCGCGCGCACCTTTCGCCGCGAAAAACGC
GCGGAACGCCTGACCAGCCGCGTGAAAGCGCTGTTTAGCGTGCTGAACTATGAACG
CGCGCGCCGCCCGGGCCTGCTGGGCGCGAGCGTGCTGGGCCTGGATGATATTCATC
GCGCGTGGCGCACCTTTGTGCTGCGCGTGCGCGCGCAGGATCCGCCGCCGGAACTGT
ATTTTGTGAAAGTGGATGTGACCGGCGCGTATGATACCATTCCGCAGGATCGCCTGA
CCGAAGTGATTGCGAGCATTATTAAACCGCAGAACACCTATTGCGTGCGCCGCTATG
CGGTGGTGCAGAAAGCGGCGCATGGCCATGTGCGCAAAGCGTTTAAAAGCCATGTG
AGCACCCTGACCGATCTGCAGCCGTATATGCGCCAGTTTGTGGCGCATCTGCAGGAA
ACCAGCCCGCTGCGCGATGCGGTGGTGATTGAACAGAGCAGCAGCCTGAACGAAGC
GAGCAGCGGCCTGTTTGATGTGTTTCTGCGCTTTATGTGCCATCATGCGGTGCGCATT
CGCGGCAAAAGCTATGTGCAGTGCCAGGGCATTCCGCAGGGCAGCATTCTGAGCAC
CCTGCTGTGCAGCCTGTGCTATGGCGATATGGAAAACAAACTGTTTGCGGGCATTCG
CCGCGATGGCCTGCTGCTGCGCCTGGTGGATGATTTTCTGCTGGTGACCCCGCATCT
GACCCATGCGAAAACCTTTCTGCGCACCCTGGTGCGCGGCGTGCCGGAATATGGCTG
CGTGGTGAACCTGCGCAAAACCGTGGTGAACTTTCCGGTGGAAGATGAAGCGCTGG
GCGGCACCGCGTTTGTGCAGATGCCGGCGCATGGCCTGTTTCCGTGGTGCGGCCTGC
TGCTGGATACCCGCACCCTGGAAGTGCAGAGCGATTATAGCAGCTATGCGCGCACC
AGCATTCGCGCGAGCCTGACCTTTAACCGCGGCTTTAAAGCGGGCCGCAACATGCG
CCGCAAACTGTTTGGCGTGCTGCGCCTGAAATGCCATAGCCTGTTTCTGGATCTGCA
GGTGAACAGCCTGCAGACCGTGTGCACCAACATTTATAAAATTCTGCTGCTGCAGGC
GTATCGCTTTCATGCGTGCGTGCTGCAGCTGCCGTTTCATCAGCAGGTGTGGAAAAA
CCCGACCTTTTTTCTGCGCGTGATTAGCGATACCGCGAGCCTGTGCTATAGCATTCTG
AAAGCGAAAAACGCGGGCATGAGCCTGGGCGCGAAAGGCGCGGCGGGCCCGCTGC
CGAGCGAAGCGGTGCAGTGGCTGTGCCATCAGGCGTTTCTGCTGAAACTGACCCGC
CATCGCGTGACCTATGTGCCGCTGCTGGGCAGCCTGCGCACCGCGCAGACCCAGCTG
```

```
-continued
AGCCGCAAACTGCCGGGCACCACCCTGACCGCGCTGGAAGCGGCGGCGAACCCGGC

GCTGCCGAGCGATTTTAAAACCATTCTGGAT

3'
```

As will be appreciated by those skilled in the art, because the recombinant plasmid is a circular vector, the one or more sequences of the mRNA expression cassettes may be connected at the 3' end of SEQ ID NO. 1, as shown in SEQ ID NO. 3 or at the 5' end of SEQ ID NO. 1.

As will be appreciated by those skilled in the art, a perfect match of nucleotides with each of the mRNA expression cassette sequences is not necessary in order to have the desired result of increased bioavailability of the target biomolecule as a result of the target cell producing the mRNA sequence that code for the expression of the target biomolecule. In some embodiments of the present disclosure, about 80% to about 100% nucleotide sequence matching with each of the mRNA expression cassettes causes the desired result. In some embodiments of the present disclosure, about 85% to about 100% nucleotide sequence matching with each of the mRNA expression cassettes causes the desired result. In some embodiments of the present disclosure, about 90% to about 100% nucleotide sequence matching with each of the mRNA expression cassettes causes the desired result. In some embodiments of the present disclosure, about 95% to about 100% nucleotide sequence matching with each of the mRNA expression cassettes causes the desired result.

Example 1—Expression Cassette

Expression cassettes for expressing mRNA were synthesized. The synthesized mRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each mRNA expression cassette was amplified by polymerase chain reaction (PCR) using Taq polymerase and the PCR products were gel purified and the bands on interest were also excised and purified using a gel extraction kit. These PCR products contained the mRNA expression cassettes in addition to 15 base pair 5' and 3' overhangs that aligned with the ends of the linearized pAVA-00200 backbone. Using in-fusion cloning, the amplified mRNA expression cassettes are integrated with the pAVA-00200 backbone via homologous recombination. The resulting RP contained the following: 5' ITR, CASI promoter, mRNA expression cassette, WPRE, SV40 polyA and ITR 3'.

The invention claimed is:

1. A composition that comprises a recombinant plasmid (RP) with an insert sequence of nucleotides that is SEQ ID NO: 3, wherein the insert sequence encodes for a sequence of messenger ribonucleic acid (mRNA) that encodes for a protein.

2. The composition of claim 1, wherein the RP is encased in a viral vector.

3. The composition of claim 2, wherein the viral vector is one of a double stranded DNA virus, a single stranded DNA virus, a single stranded RNA virus, or a double stranded RNA virus.

4. The composition of claim 2, wherein the viral vector is an adeno-associated virus.

5. The composition of claim 1, wherein the protein is telomerase reverse transcriptase (TERT).

6. The composition of claim 1, wherein the RP is encased in a protein coat, a lipid vesicle, or any combination thereof.

* * * * *

SEQUENCE LISTING

```
Sequence total quantity: 3
SEQ ID NO: 1             moltype = DNA   length = 5200
FEATURE                  Location/Qualifiers
source                   1..5200
                         mol_type = other DNA
                         organism = synthetic construct
SEQUENCE: 1
ttctagaaag atctaacttg tttattgcag cttataatgg ttacaaataa agcaatagca   60
tcacaaattt cacaaataaa gcatttttt cactgcattc tagttgtggt ttgtccaaac  120
tcatcaatgt atcttatcat gtctggatct cgacctgcac tagagcatgg ctacgtagat  180
aagtagcatg gcgggttaat cattaactac aaggaacccc tagtgatgga gttgccact   240
ccctctctgc gcgctcgctc gctcactgag gccgggcgac caaaggtcgc ccgacgcccg  300
ggctttgccc gggcggcctc agtgagcgag cgagcgcgca gctggcgtaa tagcgaagag  360
gcccgcaccg atcgcccttc ccaacagttg cgcagcctga atggcgaatg gcgattccgt  420
tgcaatggct ggcggtaata ttgttctgga tattaccagc aaggccgata gtttgagttc  480
ttctactcag gcaagtgatg ttattactaa tcaaagaagt attgcgacaa cggttaattt  540
gcgtgatgga cagactcttt tactcggtgg cctcactgat tataaaaaca cttctcagga  600
ttctggcgta ccgttcctgt ctaaaatccc tttaatcggc ctcctgttta gctcccgctc  660
tgattctaac gaggaaagca cgttatacgt gctcgtcaaa gcaaccatag tacgcgccct  720
gtagcggcgc attaagcgcg gcgggtgtgg tggttacgcg cagcgtgacc gctacacttg  780
ccagcgccct agcgcccgct cctttcgctt tcttcccttc ctttctcgcc acgttcgccg  840
gctttccccg tcaagctcta aatcgggggc tccctttagg gttccgattt agtgctttac  900
ggcacctcga ccccaaaaaa cttgattagg gtgatggttc acgtagtggg ccatcgccct  960
gatagacggt ttttcgccct tgacgttgga gtccacgtt ctttaatagt ggactcttgt  1020
tccaaactgg aacaacactc aaccctatct cggtctattc ttttgattta aagggattt   1080
tgccgatttc ggcctattgg ttaaaaatg agctgattta acaaaaattt aacgcgaatt  1140
ttaacaaaat attaacgttt acaatttaaa tatttgctta tacaatcttc ctgttttggg  1200
ggcttttctg attatcaacc ggggtacata tgattgacat gctagttta cgattaccgt  1260
tcatcgattc tcttgtttgc tccagactct caggcaatga cctgatagcc tttgtagaga  1320
cctctcaaaa atagctaccc tctccggcat gaatttatca gctagaacgg ttgaatatca  1380
tattgatggt gatttgactg tctccggcct ttctcacccg tttgaatctt tacctacaca  1440
ttactcaggc attgcattta aaatatatga gggttctaaa aatttttatc cttgcgttga  1500
aataaaggct tctcccgcaa aagtattaca gggtcataat gtttttggta caaccgattt  1560
agctttatgc tctgaggctt tattgcttaa ttttgctaat tctttgcctt gcctgtatga  1620
tttattggat gttggaattc ctgatgcggt attttctcct tacgcatctg tgcggtattt  1680
cacaccgcat atggtgcact ctcagtacaa tctgctctga tgccgcatag ttaagccagc  1740
cccgacaccc gccaacaccc gctgacgcgc cctgacgggc ttgtctgctc ccggcatccg  1800
cttacagaca agctgtgacc gtctccggga gctgcatgtg tcagaggttt tcaccgtcat  1860
```

```
caccgaaacg cgcgagacga aagggcctcg tgatacgcct atttttatag gttaatgtca 1920
tgataataat ggtttcttag acgtcaggtg gcacttttcg gggaaatgtg cgcggaaccc 1980
ctatttgttt atttttctaa atacattcaa atatgtatcc gctcatgaga caataaccct 2040
gataaatgct tcaataatat tgaaaaagga agagtatgag tattcaacat ttccgtgtcg 2100
cccttattcc cttttttgcg gcattttgcc ttcctgtttt tgctcaccca gaaacgctgg 2160
tgaaagtaaa agatgctgaa gatcagttgg gtgcacgagt gggttacatc gaactggatc 2220
tcaacagcgg taagatcctt gagagttttc gccccgaaga acgttttcca atgatgagca 2280
cttttaaagt tctgctatgt ggcgcggtat tatcccgtat tgacgccggg caagagcaac 2340
tcggtcgccg catacactat tctcagaatg acttggttga gtactcacca gtcacagaaa 2400
agcatcttac ggatggcatg acagtaagag aattatgcag tgctgccata accatgagtg 2460
ataacactgc ggccaactta cttctgacaa cgatcggagg accgaaggag ctaaccgctt 2520
ttttgcacaa catgggggat catgtaactc gccttgatcg ttgggaaccg gagctgaatg 2580
aagccatacc aaacgacgag cgtgacacca cgatgcctgt agcaatggca acaacgttgc 2640
gcaaactatt aactggcgaa ctacttactc tagcttcccg gcaacaatta atagactgga 2700
tggaggcgga taaagttgca ggaccacttc tgcgctcggc ccttccggct ggctggttta 2760
ttgctgataa atctggagcc ggtgagcgtg ggtctcgcgg tatcattgca gcactggggc 2820
cagatggtaa gccctcccgt atcgtagtta tctacacgac ggggagtcag gcaactatgg 2880
atgaacgaaa tagacagatc gctgagatag gtgcctcact gattaagcat tggtaactgt 2940
cagaccaagt ttactcatat atactttaga ttgatttaaa acttcatttt taatttaaaa 3000
ggatctaggt gaagatcctt tttgataatc tcatgaccaa aatcccttaa cgtgagtttt 3060
cgttccactg agcgtcagac cccgtagaaa agatcaaagg atcttcttga gatccttttt 3120
ttctgcgcgt aatctgctgc ttgcaaacaa aaaaaccacc gctaccagcg gtggtttgtt 3180
tgccggatca agagctacca actctttttc cgaaggtaac tggcttcagc agagcgcaga 3240
taccaaatac tgtccttcta gtgtagccgt agttaggcca ccacttcaag aactctgtag 3300
caccgcctac atacctcgct ctgctaatcc tgttaccagt ggctgctgcc agtggcgata 3360
agtcgtgtct taccgggttg gactcaagac gatagttacc ggataaggcg cagcggtcgg 3420
gctgaacggg gggttcgtgc acacagccca gcttggagcg aacgacctac accgaactga 3480
gatacctaca gcgtgagcta tgagaaagcg ccacgcttcc cgaagggaga aaggcggaca 3540
ggtatccggt aagcggcagg gtcggaacag gagagcgcac gagggagctt ccaggggaa  3600
acgcctggta tctttatagt cctgtcgggt ttcgccacct ctgacttgag cgtcgatttt 3660
tgtgatgctc gtcaggggg cggagcctat ggaaaaacgc cagcaacgcg gcctttttac 3720
ggttcctggc cttttgctgg ccttttgctc acatgttctt tcctgcgtta tcccctgatt 3780
ctgtggataa ccgtattacc gcctttgagt gagctgatac cgctcgccgc agccgaacga 3840
ccgagcgcag cgagtcagtg agcgaggaag cggaagagcg cccaatacgc aaaccgcctc 3900
tccccgcgcg ttggccgatt cattaatgca gctgcgcgct cgctcgctca ctgaggccgc 3960
ccgggcaaag cccgggcgtc gggcgacctt tggtcgcccg gcctcagtga gcgagcgagc 4020
gcgcagagag ggagtggcca actccatcac taggggttcc ttgtagttaa tgattaaccc 4080
gccatgctac ttatctacgt agccatgctc taggacattg attattgact agtggagttc 4140
cgcgttacat aacttacggt aaatggcccg cctggctgac cccccgccca 4200
ttgacgtcaa taatgacgta tgttcccata gtaacgccaa tagggacttt ccattgacgt 4260
caatgggtgg agtatttacg gtaaactgcc cacttggcag tacatcaagt gtatcatatg 4320
ccaagtacgc cccctattga cgtcaatgac ggtaaatggc ccgcctggca ttatgcccag 4380
tacatgacct tatgggactt tcctacttgg cagtacatct acgtattagt catcgctatt 4440
accatggtcg aggtgagccc cacgttctgc ttcactctcc ccatctcccc ccctccccca 4500
cccccaattt tgtatttatt tattttttaa ttattttgtg cagcgatggg ggcggggggg 4560
ggggggggcg cgcgccaggc ggggcgggc ggggcgaggg gcgggcggg gcgaggcgga 4620
gaggtgcggc ggcagccaat cagagcggcg cgctccgaaa gtttccttt atggcgaggc 4680
ggcggcggcg gcggccctat aaaaagcgaa gcgcgcggcg ggcgggagtc gctgcgcgct 4740
gccttcgccc cgtgccccgc tccgccgccg cctcgcgccg cccgccccgg ctctgactga 4800
ccgcgttact aaaacaggta agtccggcct ccgcgccggg ttttggcgcc tcccgcgggc 4860
gcccccctcc tcacggcgag cgctgccacg tcagacgaag ggcgcagcga gcgtcctgat 4920
ccttccgccc ggacgctcag gacagcggcc cgctgctcat aagactcggc cttagaaccc 4980
cagtatcagc agaaggacat tttaggacgg gacttgggtg actctagggc actgttttc  5040
tttccagaga gcgaacagg cgaggaaaag tagtcccttc tcggcgattc tgcggaggga 5100
tctccgtggg gcggtgaacg ccgatgatgc ctctactaac catgttcatg ttttctttt  5160
ttttctacag gtcctgggtg acgaacaggg taccgccacc              5200
SEQ ID NO: 2           moltype = DNA   length = 3395
FEATURE                Location/Qualifiers
source                 1..3395
                       mol_type = other DNA
                       organism = synthetic construct
SEQUENCE: 2
atgccgcgcg cgccgcgctg ccgcgcggtg cgcagcctgc tgcgcagcca ttatcgcgaa 60
gtgctgccgc tggcgacctt tgtgcgccgc ctgggcccgc agggctggcg cctggtgcag 120
cgcggcgatc cggcggcgtt tcgcgcgctg gtggcgcagt gctggtgtg cgtgccgtgg 180
gatgcgcgcc cgccgccggc ggcgccgagc tttcgccagg tgagctgcct gaaagaactg 240
gtggcgcgcg tgctgcagcg cctgtgcgaa cgcgcgcga aaacgtgct ggcgtttggc 300
tttgcgtgct ggatggcgc gcgcgggcc ccgccgaagg cgtttaccac cagcgtgcgc 360
agctatctgc cgaacaccgt gaccgatgcg tgccgggcag cggcgcgtgg ggcctgctgc 420
tgcgccgcgt gggcgatgat gtgctggtgc atctgctggc gcgctgcgcg ctgtttgtgc 480
tggtggcgcc gagctgcgcg tatcaggtgt gcggcccgcc gctgtatcag ctgggcgcgg 540
cgacccaggc gcgcccgccg ccgcatgcga gcggcccgcc ccgccgcctg gctgcgaac  600
gcgcgtggaa ccatagcgtg cgcgaagcgg gcgtgccgcc gggcctgccg cgcgaaacgc 660
cgcgccgccg cggcggcagc gcgagccgca gcctgcgcct gccgaaacgc ccgccgccgc 720
gcgcggcgcc ggaaccggaa cgcacccccg tgggccaggg cagctggcg catccgggcc 780
gcacccgcgc cccgagcgat cgcggcttt cgtggtgag cccggcgcgc ccggcggaag 840
aagcgaccag cctggaaggc gcgctgagcg gcacccgcca tagccatccg agcgtgggcc 900
gccagcatca tgcgggcccg ccgagcacca gccgcccgcc gcgcccgtgg gatacccgt  960
```

```
gcccgccggt gtatgcggaa accaaacatt ttctgtatag cagcggcgat aaagaacagc  1020
tgcgcccgag ctttctgctg agcagcctgc gcccgagcct gaccggcgcg cgccgcctgg  1080
tggaaaccat ttttctgggc agccgcccgt ggatgccggg caccccgcgc cgcctgccgc  1140
gcctgccgca gcgctattgg cagatgcgcc cgctgtttct ggaactgctg ggcaaccatg  1200
cgcagtgccc gtatggcgtg ctgctgaaaa cccattgcgc gctggcgcgc gcggtgaccc  1260
cggcggcggg cgtgtgcgcg cgcgaaaaac cgcagggcag cgtggcggcg ccggaagaag  1320
aagataccga tccgcgccgc ctggtgcagc tgctgcgcca gcatagcagc ccgtggcagg  1380
tgtatgcgct tgtgcgcgcg tgcctgcgcc gcctggtgcc gccgggcctg tggggcagcc  1440
gccataacga acgccgcttt ctgcgcaaca ccaaaaaatt tattagccgg ggcaaacatg  1500
cgaaactgag cctgcaggaa ctgacctgga aaatgagcgt gcgcgattgc gcgtggctgc  1560
gccgcagccc gggcgtgggc tgcgtgccgg cggcggaaca tcgcctgcgc gaagaaattc  1620
tggcgaaatt tctgcattgg ctgatgagcg tgtatgtggt ggaactgctg cgcagctttt  1680
tttatgtgac cgaaaccacc tttcagaaaa accgcctgtt tttttatcgc aaaagcgtgt  1740
ggagcaaact gcagagcatt ggcattcgcc agcatctgaa acgcgtgcag ctgcgcgaac  1800
tgagcgaagc ggaagtgcgc cagcatcgcg aagcgcgccc ggcgctgctg accagccgcc  1860
tgcgctttat tccgaaaccg gatggcctgc gcccgattgt gaacatggat tatgtggtgg  1920
gcgcgcgcac ctttcgccgc gaaaaacgcg cggaacgcct gaccagccgc gtgaaagcgc  1980
tgtttagcgt gctgaactat gaacgcgcgc gccgcccggg cctgctgggc gcgagcgtgc  2040
tgggcctgga tgatattcat cgcgcgtggc gcacctttgt gctgcgcgtg cgcgcgcagg  2100
atccgccgcc ggaactgtat tttgtgaaag tggatgtgac cggcgcgtat gataccattc  2160
cgcaggatcc gcctgaccgaa gtgattgcga gcattattaa accgcagaac acctattgcg  2220
tgcgccgcta tgcggtggtg cagaaagcgg cgcatgccca tgtgcgcaaa gcgtttaaaa  2280
gccatgtgag caccctgacc gatctgcagc cgtatatgcg ccagtttgtg gcgcatctgc  2340
aggaaaccag cccgctgcgc gatgcggtgg tgattgaaca gagcagcagc ctgaacgaag  2400
cgagcagcgg cctgtttgat gtgtttctgc gctttatgtg ccatcatgcg gtgcgcattc  2460
gcggcaaaag ctatgtgcag tgccagggca ttccgcagca ttctg agcaccctgc  2520
tgtgcagcct gtgctatggc gatatgcgaaa acaaactgtt tgcgggcatt cgccgcgatg  2580
gcctgctgct gcgcctggtg gatgattttc tgctggtgac cccgcatctg acccatgcga  2640
aaaccttctct gcgcaccctg gtgcgcgcg tgccggaata tggctgcgtg gtgaacctgc  2700
gcaaaaccgt ggtgaacttt ccggtggaag atgaagcgct gggcggcacc gcgtttgtgc  2760
agatgccggc gcatggcctg tttccgtggt gcggcctgct gctggatacc cgcaccctgg  2820
aagtgcagag cgattatagc agctatgcgc gcaccagcat tcgcgcgagc ctgacccttta  2880
accgcggctt taaagcgggc cgcaacatgc cgcaaact gtttggcgtg ctgcgcctga  2940
aatgccatag cctgtttctg gatctgcagg tgaacaccat gcagaccgtg tgcaccaaca  3000
tttataaaat tctgctgctg caggcgtatc gctttcatgc gtgcgtgctg cagctgccgt  3060
ttcatcagca ggtgtggaaa acccgacctt tttttctgcg cgtgattagc gataccgcga  3120
gcctgtgcta tagcattctg aaagcgaaaa acgcgggcat gagcctgggc gcgaaaggcg  3180
cggcgggccc gctgccgagc gaagcggtgc agtggctgtg ccatcaggcg tttctgctga  3240
aactgacccg ccatcgcgtg acctatgtgc cgctgctggg cagcctgcgc accgcgcaga  3300
cccagctgag ccgcaaactg ccgggcacca ccctgaccgg gctggaagcg gcggcgaacc  3360
cggcgctgcc gagcgatttt aaaaccattc tggat                              3395
```

SEQ ID NO: 3      moltype = DNA  length = 8595
FEATURE              Location/Qualifiers
source               1..8595
                     mol_type = other DNA
                     organism = synthetic construct
SEQUENCE: 3

```
ttctagaaag atcaacttg tttattgcag cttataatgg ttacaaataa agcaatagca   60
tcacaaattt cacaaataaa gcatttttt cactgcattc tagttgtggt ttgtccaaac  120
tcatcaatgt atcttatcat gtctggatct cgacctcgac tagagcatgg ctacgtagat  180
aagtagcatg gcgggttaat cattaactac aaggaaccc tagtgatgga gttggcact   240
ccctctctgc gcgctcgctc gctcactgag gccgggcgac caaaggtcgc ccgacgcccg  300
ggctttgccc gggcggcctc agtgagcgag cgagcgcgca gctggcgtaa tagcgaagag  360
gcccgcaccg atcgcccttc ccaacagttg cgcagcctga atggcgaatg gcgattccgt  420
tgcaatggct ggcggtaata ttgttctgga tattaccagc aaggccgata gtttgagttc  480
ttctactcag gcaagtgatg ttattactaa tcaaagaagt attgcgacaa cggttaattt  540
gcgtgatgga cagactcttt tactcggtgg cctcactgat tataaaaaca cttctcagga  600
ttctggcgta ccgttcctgt ctaaaatccc tttaatcggc ctcctgttta gctcccgctc  660
tgattctaac gaggaaagca cgttatacgt gctcgtcaaa gcaaccatag tacgcgccct  720
gtagcggcgc attaagcgcg gcgggtgtgg tggttacgcg cagcgtgacc gctacacttg  780
ccagcgccct agcgcccgct cctttcgctt tcttccttc ctttctcgcc acgttcgccg  840
gctttccccg tcaagctcta aatcgggggc tccctttagg gttccgattt agtgctttac  900
ggcacctcga ccccaaaaaa cttgattagg gtgatggttc acgtagtggg ccatcgccct  960
gatagacggt ttttcgccct tgacgttgg agtccacgtt ctttaatagt ggactcttgt 1020
tccaaactgg aacaacactc aaccctatct cggtctattc ttttgattta agggattt  1080
tgccgatttc ggcctattgg ttaaaaaatg agctgattta caaaaattt aacgcgaatt  1140
ttaacaaaat attaacgttt acaatttaaa tatttgctta taacatcttc ctgttttggg  1200
ggcttttctg attatcaacc ggggtacata tgattgacat gctagtttta cgattaccgt  1260
tcatcgattc tcttgtttgc tccagactct caggcaatga cctgatagcc tttgtagaga  1320
cctctcaaaa atagctaccc tctccggcat gaatttatca gctagaacgg ttgaatatca  1380
tattgatggt gatttgactg tctccggcct ttctcacccg tttgaatctt tacctacaca  1440
ttactcaggc attgcatta aaatatgat gggttcaaa aatttttatc cttgcgttga  1500
aataaaggct tctcccgcaa aagtattaca gggtcataat gtttttggta caaccgattt  1560
agctttatgc tctgaggctt tattgcttaa tttttgctaat tctttgcctt gcctgtatga  1620
tttattggat gttggaattc ctgatgcggt attttctcct tacgcatctg tgcggtattt  1680
cacaccgcat atggtgcact ctcagtacaa tctgctctga tgccgcatag ttaagccagc  1740
cccgacaccc gccaacaccc gctgacgcgc cctgacgggc ttgtctgctc ccggcatccg  1800
cttacagaca agctgtgacc gtctccggga gctgcatgtg tcagaggttt tcaccgtcat  1860
```

```
caccgaaacg cgcgagacga aagggcctcg tgatacgcct atttttatag gttaatgtca 1920
tgataataat ggtttcttag acgtcaggtg gcacttttcg gggaaatgtg cgcggaaccc 1980
ctatttgttt attttttctaa atacattcaa atatgtatcc gctcatgaga caataaccct 2040
gataaatgct tcaataatat tgaaaaagga agagtatgag tattcaacat ttccgtgtcg 2100
cccttattcc cttttttgcg gcattttgcc ttcctgtttt tgctcaccca gaaacgctgg 2160
tgaaagtaaa agatgctgaa gatcagttgg gtgcacgagt gggttacatc gaactggatc 2220
tcaacagcgg taagatcctt gagagttttc gccccgaaga acgttttcca atgatgagca 2280
cttttaaagt tctgctatgt ggcgcggtat tatcccgtat tgacgccggg caagagcaac 2340
tcggtcgccg catacactat tctcagaatg acttggttga gtactcacca gtcacagaaa 2400
agcatcttac ggatggcatg acagtaagag aattatgcag tgctgccata accatgagtg 2460
ataacactgc ggccaactta cttctgacaa cgatcggagg accgaaggag ctaaccgctt 2520
ttttgcacaa catgggggat catgtaactc gccttgatcg ttgggaaccg gagctgaatg 2580
aagccatacc aaacgacgag cgtgacacca cgatgcctgt agcaatggca acaacgttgc 2640
gcaaactatt aactggcgaa ctacttactc tagcttcccg gcaacaatta atagactgga 2700
tggaggcgga taaagttgca ggaccacttc tgcgctcggc ccttccggct ggctggttta 2760
ttgctgataa atctggagcc ggtgagcgtg ggtctcgcgg tatcattgca gcactggggc 2820
cagatggtaa gccctcccgt atcgtagtta tctacacgac ggggagtcag gcaactatgg 2880
atgaacgaaa tagacagatc gctgagatag gtgcctcact gattaagcat tggtaactgt 2940
cagaccaagt ttactcatat atactttaga ttgatttaaa acttcatttt taatttaaaa 3000
ggatctaggt gaagatcctt tttgataatc tcatgaccaa aatcccttaa cgtgagtttt 3060
cgttccactg agcgtcagac cccgtagaaa agatcaaagg atcttcttga gatccttttt 3120
ttctgcgcgt aatctgctgc ttgcaaacaa aaaaaccacc gctaccagcg gtggttttgt 3180
tgccggatca agagctacca actctttttc cgaaggtaac tggcttcagc agagcgcaga 3240
taccaaatac tgtccttcta gtgtagccgt agttaggcca ccacttcaag aactctgtag 3300
caccgcctac atacctcgct ctgctaatcc tgttaccagt ggctgctgcc agtggcgata 3360
agtcgtgtct taccgggttg gactcaagac gatagttacc ggataaggcg cagcggtcgg 3420
gctgaacggg gggttcgtgc acacagccca gcttggagcg aacgacctac accgaactga 3480
gatacctaca gcgtgagcta tgagaaagcg ccacgcttcc cgaagggaga aaggcggaca 3540
ggtatccggt aagcggcagg gtcggaacag gagagcgcac gagggagctt ccaggggaa 3600
acgcctggta tctttatagt cctgtcgggt ttcgccacct ctgacttgag cgtcgatttt 3660
tgtgatgctc gtcaggggg cggagcctat ggaaaaacgc cagcaacgcg gccttttac 3720
ggttcctggc cttttgctgg ccttttgctc acatgttctt tcctgcgtta tcccctgatt 3780
ctgtggataa ccgtattacc gcctttgagt gagctgatac cgctcgccgc agccgaacga 3840
ccgagcgcag cgagtcagtg agcgaggaag cggaagagcg cccaatacgc aaaccgcctc 3900
tccccgcgcg ttggccgatt cattaatgca gctgcgcgct cgctcgtca ctgaggccgc 3960
ccgggcaaag cccgggcgtc gggcgacctt tggtcgcccg gcctcagtga gcgagcgagc 4020
gcgcagagag ggagtggcca actccatcac taggggttcc ttgtagttaa tgattaaccc 4080
gccatgctac ttatctacgt agccatgctc taggacattg attattgact agtggagttc 4140
cgcgttacat aacttacggt aaatggcccg cctggctgac cgcccaacga cccccgccca 4200
ttgacgtcaa taatgacgta tgttcccata gtaacgccaa tagggacttt ccattgacgt 4260
caatgggtgg agtatttacg gtaaactgcc cacttggcag tacatcaagt gtatcatatg 4320
ccaagtacgc cccctattga cgtcaatgac ggtaaatggc ccgcctggca ttatgcccag 4380
tacatgacct tatgggactt tcctacttgg cagtacatct acgtattagt catcgctatt 4440
accatggtcg aggtgagccc cacgttctgc ttcactctcc ccatctcccc cccctcccca 4500
cccccaattt tgtatttatt tattttttaa ttattttgtg cagcgatggg ggcgggggg 4560
ggggggggcg cgcgccaggc ggggcgggggc ggggcgaggg gcgggcggg gcgaggcgga 4620
gaggtgcggc ggcagccaat cagagcggcg cgctccgaaa gtttcctttt atggcgaggc 4680
ggcggcggcg gcgcccctat aaaaagcgaa gcgcgcggcg ggcggagtc gctgcgcgct 4740
gccttcgccc cgtgccccgc tccgccgcg cctcgcgccg cccgccccgg ctctgactga 4800
ccgcgttact aaaacaggta agtccggcct ccgcgccggg ttttggcgcc tcccgcgggc 4860
gcccccctcc tcacggcgag cgctgccacg tcagacgaag ggcgcagcga gcgtcctgat 4920
ccttccgccc ggacgctcag gacagcggcc cgctgctcat aagactcggc cttagaaccc 4980
cagtatcagc agaaggacat ttaggacgg gacttgggtg actctagggc actggttttc 5040
tttccagaga gcgaacagg cgaggaaaag tagtcccttc tcggcgattc tgcggaggga 5100
tctccgtggg gcggtgaacg ccgatgatgc ctctactaac catgttcatg tttctttttt 5160
ttttctacag gtcctgggtg acgaacaggg taccgccacc atgccgcgcg cgccgcgctg 5220
ccgcgcggtg cgcagcctgc tgcgcagcca ttatcgcgaa gtgctgccgc tggcgacctt 5280
tgtgcgccgc ctgggcccgc agggctggcc cctggtgcag cgcggcgatc cggcggcgtt 5340
tcgcgcgctg gtggcgcagt gcctggtgtg cgtgccgtgg gatgcgcgc cgcgccggc 5400
ggcgccgagc tttcgcagg tgagctgcct gaaagaactg gtggcgcgcg tgctgcagg 5460
cctgtgcgaa cgcggcgcga aaaacgtgct ggcgtttgg tttgcgctgc tggatgcgc 5520
gcgcggcggc cgccggaag cgtttaccac cagcgtgcgc agctatctgc gaacaccgt 5580
gaccgatgcg tgcgcggcag cggcgcgtgg ggcctgctgc tgcgccgcgt gggcgatgat 5640
gtgctggtgc atctgctggc gcgctgcgcg ctgttgtgc tggtggcgc gagctgcgg 5700
tatcaggtgt gcggcccgcc gctgtatcag ctgggcgcg cgaccaggc gcgcccgcg 5760
ccgcatgcga gcggccgcg ccgcctgct ggctgcgaac gcgcgtggaa ccatagcgtg 5820
cgcgaagcgg gcgtgccgct gggcctgccg gcgccgggcg cgcgccgccg cggcggcagc 5880
gcgagccgca ggcctgccgct gccgaaacgc ccgccgccgc gcgcggcgcc ggaaccggaa 5940
cgcaccccgg tgggccaggg cagtccggcg catccggccg cccgagccgat 6000
cgcggctttt gcgtggtgag cccggcgcgc ccggcggaag aagcgaccag cctggaaggc 6060
gcgctgagcg gcaccggcca tagccatccg agcgtgggcc gccagcatca tgcgggcccg 6120
ccgagcacca gccgccgcc gcgccgtgg gataccccgt gcccgccggt gtatgcgaa 6180
accaaacatt ttctgtatag cagcggcgat aaagaacagc tgcgcccgag cttctgctg 6240
agcagcctgc gcccgagcct gaccgcgcg cgccgcctgg tggaaaccat ttttctgggc 6300
agccgccgtc ggatgccggg caccccgcgc cgcctgccgc gcctgccgca gcgctattgg 6360
cagatgcgcc cgctgtttct ggaactgctg gcaaccatg cgcagtgccc gtatgcgtg 6420
ctgctgaaaa cccattgccc gctgcgcgcg cggtgaccc cggcggcggg cgtgtgcgcg 6480
cgcgaaaaac cgcagggcag cgtggcggcg ccggaagaag aagataccga tccgcgccgc 6540
ctggtgcagc tgctgcgcca gcatagcagc ccgtggcagg tgtatggctt tgtgcgcgcg 6600
```

```
tgcctgcgcc gcctggtgcc gccgggcctg tggggcagcc gccataacga acgccgcttt    6660
ctgcgcaaca ccaaaaaatt tattagcctg ggcaaacatg cgaaactgag cctgcaggaa    6720
ctgacctgga aaatgagcgt gcgcgattgc gcgtggctgc gccgcagccc gggcgtgggc    6780
tgcgtgccgg cggcggaaca tcgcctgcgc gaagaaattc tggcgaaatt tctgcattgg    6840
ctgatgagcg tgtatgtggt ggaactgctg cgcagctttt tttatgtgac cgaaaccacc    6900
tttcagaaaa accgcctgtt tttttatcgc aaaagcgtgt ggagcaaact gcagagcatt    6960
ggcattcgcc agcatctgaa acgcgtgcag ctgcgcgaac tgagcgaagc ggaagtgcgc    7020
cagcatcgcg aagcgcgccc ggcgctgctg accagccgcc tgcgctttat tccgaaaccg    7080
gatggcctgc gcccgattgt gaacatggat tatgtggtgg gcgcgcgcac ctttcgccgc    7140
gaaaaacgcg cggaacgcct gaccagccgc gtgaaagcgc tgtttagcgt gctgaactat    7200
gaacgcgcgc gccgcccggg cctgctgggc gcgagcgtgc tgggcctgga tgatattcat    7260
cgcgcgtggc gcacctttgt gctgcgcgtg cgcgcgcagg atccgccgcc ggaactgtat    7320
tttgtgaaag tggatgtgac cggcgcgtat gataccattc cgcaggatcg cctgaccgaa    7380
gtgattgcga gcattattaa accgcagaac acctattgcg tgccgcta   tgcggtggtg    7440
cagaaagcgg cgcatggcca tgtgcgcaaa gcgtttaaaa gccatgtgag cacccctgacc   7500
gatctgcagc cgtatatgcg ccagtttgtg gcgcatctgc aggaaaccag cccgctgcgc    7560
gatgcggtgg tgattgaaca gagcagcagc ctgaacgaag cgagcagcgg cctgtttgat    7620
gtgtttctgc gctttatgtg ccatcatgcg gtgcgcattc gcgcaaaag  ctatgtgcag    7680
tgccagggca ttccgcaggg cagcattctg agcaccctgc tgtgcagcct gtgctatggc    7740
gatatgcgaaa acaaactgtt tgcgggcatt cgccgcgatg gcctgctgct gcgcctggtg    7800
gatgattttc tgctggtgac cccgcatctg acccatgcga aaacctttct gcgcaccctg    7860
gtgcgcggcg tgccggaata tggctgcgtg gtgaacctgc gcaaaaccgt ggtgaactt     7920
ccggtggaag atgaagcgct gggcggcacc gcgtttgtgc agatgccggc gcatggcctg    7980
tttccgtggt gcggcctgct gctggatacc cgcaccctgg aagtgcagag cgattatagc    8040
agctatgcgc gcaccagcat tcgcgcgagc ctgacctta   accgcggctt taaagcgggc    8100
cgcaacatgc gccgcaaact gttttggcgtg ctgcgcctga aatgccatag cctgttctg    8160
gatctgcagg tgaacagcct gcagaccgtg tgcaccaaca tttataaaat tctgctgctg    8220
caggcgtatc gctttcatgc gtgcgtgctg cagctgccgt ttcatcagca ggtgtggaaa    8280
aacccgacct tttttctgcg cgtgattagc gataccgcga gcctgtgcta tagcattctg    8340
aaagcgaaaa acgcgggcat gagcctgggc gcgaaaggcg cggcgggccc gctgccgagc    8400
gaagcggtgc agtggctgtg ccatcaggcg tttctgctga aactgacccg ccatcgcgtg    8460
acctatgtgc cgctgctggg cagcctgcgc accgcgcaga cccagctgag ccgcaaactg    8520
ccgggcacca ccctgaccgc gctggaagcg gcggcgaacc cggcgctgcc gagcgatttt    8580
aaaaccattc tggat                                                    8595
```